(12) United States Patent
Wendler et al.

(10) Patent No.: US 8,177,735 B2
(45) Date of Patent: May 15, 2012

(54) CARDIOTOMY AND VENOUS BLOOD RESERVOIR AND METHOD

(75) Inventors: Mark E. Wendler, St. Louis Park, MN (US); Ana R. Menk, Minneapolis, MN (US); Eric R. Fox, Prior Lake, MN (US); Ningze Sun, Shoreview, MN (US); Timothy D. Groen, North Branch, MN (US); Walt L. Carpenter, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 399 days.

(21) Appl. No.: 12/372,362

(22) Filed: Feb. 17, 2009

(65) Prior Publication Data

US 2010/0211028 A1  Aug. 19, 2010

(51) Int. Cl.
*A61M 37/00* (2006.01)
*C02F 1/44* (2006.01)

(52) U.S. Cl. ........... 604/6.15; 604/6.09; 210/645
(58) Field of Classification Search ............ 604/4.01, 604/5.01, 6.01, 6.09, 6.15; 210/645
See application file for complete search history.

(56) References Cited

U.S. PATENT DOCUMENTS

| | | | |
|---|---|---|---|
| 5,039,430 A | 8/1991 | Corey, Jr. | |
| 5,403,273 A * | 4/1995 | Lindsay | ................... 604/6.14 |
| 5,667,485 A | 9/1997 | Lindsay | |
| 5,800,721 A | 9/1998 | McBride | |
| 5,823,986 A | 10/1998 | Peterson | |
| 5,919,153 A | 7/1999 | Van Driel | |
| 6,183,453 B1 | 2/2001 | Swisher | |
| 6,322,546 B1 * | 11/2001 | Steg | .................... 604/319 |
| 6,908,446 B2 * | 6/2005 | Yokoyama et al. | .......... 604/6.09 |

FOREIGN PATENT DOCUMENTS

| | | |
|---|---|---|
| EP | 1464349 A1 | 10/2004 |
| WO | 9507725 A1 | 3/1995 |
| WO | 9820957 A1 | 5/1998 |
| WO | 0069618 A1 | 11/2000 |

OTHER PUBLICATIONS

International Search Report for PCT/US2010/023478 mailed May 20, 2010.

* cited by examiner

*Primary Examiner* — Leslie Deak

(57) ABSTRACT

A cardiotomy and venous blood reservoir including a housing assembly, a downtube, and a bowl. The housing assembly forms a chamber. The downtube extends from an inlet port to a downstream end within the chamber. A diameter of the tube lumen increases to the downstream end. The bowl forms a floor surface shoulder, intermediate segment, and protrusion. The shoulder circumferentially surrounds, and is spatially above, the downstream end. The intermediate segment extends radially inwardly and downwardly from the shoulder to a bottom face. The protrusion extends radially inwardly and upwardly from the bottom face to a center that is aligned with the lumen and below the downstream end. The flared inner diameter of the lumen reduces fluid velocity as venous blood enters the reservoir. The bowl floor surface gently receives the incoming venous blood at the protrusion, and smoothly guides the blood flow.

22 Claims, 9 Drawing Sheets

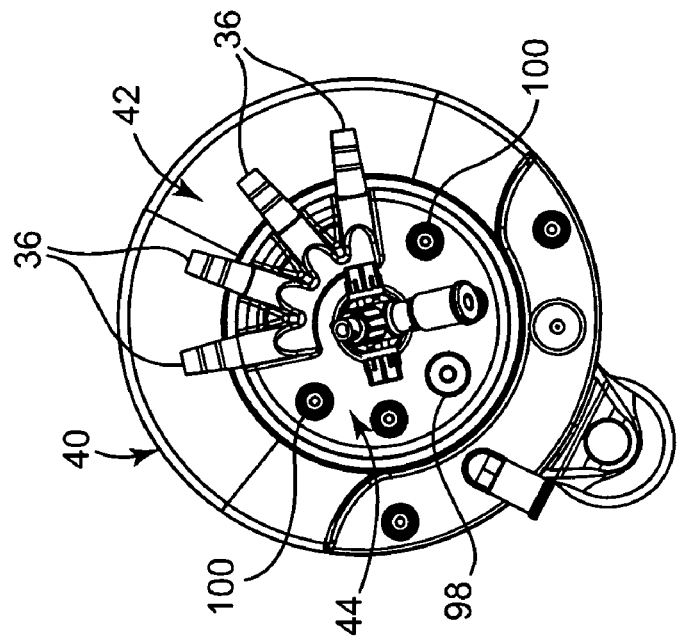
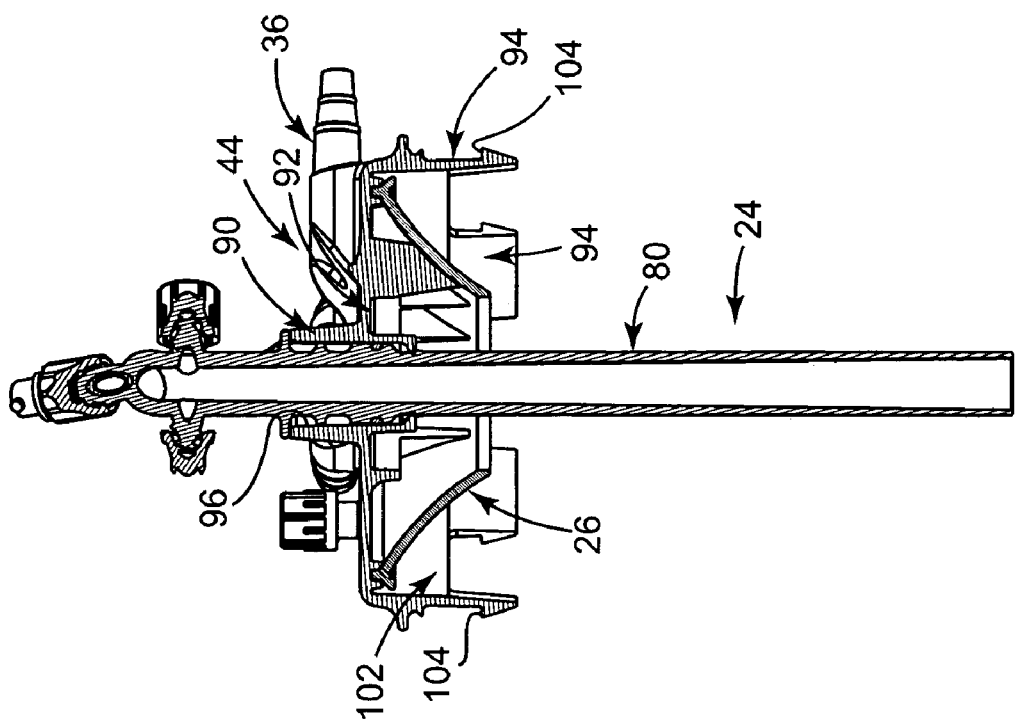
Fig. 3B
Fig. 3A

CARDIOTOMY AND VENOUS BLOOD RESERVOIR AND METHOD

BACKGROUND

The present disclosure relates to combined cardiotomy and venous return reservoirs. More particularly, it relates to cardiotomy and venous blood reservoirs with improved air handling and useful with various perfusion systems, for example in connection with patients requiring lower flow capacities.

In many surgical procedures, the functions of the heart and lungs are performed outside of the body by specialized devices such as membrane oxygenators, cardiac assist pumps, and heat exchangers. This array of equipment is operated by a perfusionist who supervises the removal and return of the patient's blood during the surgical procedure. The patient's blood is stored in a venous reservoir interposed between the vena cava tap and the pump of the heart-lung machine, which pumps the blood through the oxygenator and back into the patient's aorta. The venous reservoir also serves as a fluid buffer in the external circulation system to smooth out variations between the blood flow available from the vena cava and the demands of the heart-lung machine pump. Because a substantial amount of blood escapes from the patient's chest cavity during the surgery, it is necessary to recover this cardiotomy blood from the operative field (e.g., cardiotomy suction). Once treated (e.g., filtered), the cardiotomy blood can also be returned to the patient. While the venous blood and the cardiotomy blood can be separately maintained, it has become conventional in recent years to combine the cardiotomy and venous blood into a single, hard shell cardiotomy and venous reservoir.

A conventional, combined cardiotomy and venous blood reservoir has two distinct fluid paths leading to a main chamber: a venous blood path and a cardiotomy blood path. The venous blood path enters the reservoir through a centrally located venous intake, and is conveyed into a defoaming chamber in which any air bubbles present in the venous blood are removed before the venous blood is discharged into the main chamber of the reservoir. The cardiotomy blood enters the reservoir through one or more cardiotomy inlets, and is conveyed through various filtering/defoaming regions where cellular and surgical debris and large amounts of air are removed from the cardiotomy blood.

While available filters and defoamers employed with cardiotomy and venous blood reservoirs are highly viable for performing necessary air bubble and particulate removal, in some instances concerns remain. With pediatric applications (and in particular neonates and infants), the blood volume and maximum flow rates through the surgical perfusion circuit are reduced (as compared to adult patients). Conventional (adult) cardiotomy and venous reservoirs may be less than optimal under these circumstances. For example, the reservoir blood flow path(s), while effectuating uniform flow at higher flow rates associated with adults, may introduce discontinuities at the lower flow rates of pediatric procedures, in turn causing undesirable formation of foam. In addition, the relatively small volume of blood within the reservoir (and elevated perfusion circuit cycle rate) increases the opportunities for turbulence and therefore trauma. More particularly, when the volume of blood is low in the reservoir chamber, a conventional cardiotomy and venous return reservoir will oftentimes subject the incoming blood flow to a splashing-type flow pattern, undesirably introducing trauma into the blood. Finally, while the use of defoamers to eliminate foam in the cardiotomy and venous blood within the reservoir is well-accepted, only foamed portions of the blood flow need to contact the defoamer. Conventional practice, however, entails blood flow continuously passing over/through the defoamer(s) and may lead to complications.

In light of the above, any improvements to combined cardiotomy and venous blood reservoirs will be well-received, especially those that address the concerns associated with the low volume and/or low flow rates associated with pediatric applications.

SUMMARY

Some aspects in accordance with principles of the present disclosure relate to a cardiotomy and venous blood reservoir including a housing assembly, a cardiotomy inlet port, a venous inlet port, a downtube, and a bowl. The housing assembly forms a main chamber. The cardiotomy inlet port is fluidly connected to the chamber. The downtube defines an upstream region, a downstream region, and a lumen extending therethrough. The upstream region extends from the venous inlet port, whereas the downstream region extends from the upstream region and terminates at a downstream end located within the chamber. In this regard, a diameter of the lumen increases along at least the downstream region to the downstream end. The bowl is disposed within the chamber and forms a floor surface facing the downstream end of the downtube, and thus receives and guides venous blood dispensed from the downstream end. In this regard, the floor surface is defined by an annular shoulder segment, an intermediate segment, and a protrusion. The shoulder segment circumferentially surrounds, and is radially spaced from, the downstream end, and is spatially located above the downstream end. The intermediate segment extends radially inwardly and downwardly from the shoulder segment to a bottom face opposite the shoulder segment. Upon final assembly, the bottom face is located spatially below the downstream end. Finally, the protrusion extends radially inwardly and upwardly from the bottom face to a center that is aligned with the lumen and is spaced below the downstream end. With this construction, the flared inner diameter of the downtube lumen reduces fluid velocity as the venous blood enters the reservoir, thus improving air handling performance. The geometry of the bowl floor surface gently receives the incoming venous blood at the protrusion, and smoothly guides the blood flow along the intermediate segment and the shoulder segment, effectively maintaining a smooth, substantially laminar flow. Further, the shoulder segment establishes a fill line of the bowl, with the downstream end of the downtube maintained below this fill line. As a result, air is prevented from entering the downtube when the flow of incoming venous blood is stopped. In some embodiments, the bowl further includes an outer rim segment extending from the shoulder segment, and leading to a venous screen filter. In related embodiments, the reservoir further includes a cardiotomy filter positioned such that cardiotomy blood flow through the cardiotomy filter is directed onto the venous filter and subsequently into the main chamber.

Yet other aspects of the present disclosure relate to a combination cardiotomy and venous blood reservoir including a housing assembly, a cardiotomy inlet port, a cardiotomy sub-assembly, a venous inlet port, and a venous sub-assembly. The housing assembly forms a main chamber. The cardiotomy sub-assembly forms an inlet side, an outlet side, and a cardiotomy chamber. The inlet side is open to the cardiotomy inlet port, whereas the outlet side is open to the main chamber. The cardiotomy chamber is formed between the inlet and outlet sides, and forms a flow surface therebetween. Further, the cardiotomy sub-assembly includes a cardiotomy filter fluidly connected to the flow surface, and a cardiotomy defoamer spaced from the flow surface. The venous sub-assembly includes a downtube, a bowl, a venous filter, and a venous defoamer. The downtube forms a lumen fluidly connected to the venous inlet port and terminating at a downstream end opposite the venous inlet port. The bowl forms a floor surface and is positioned to receive venous blood dispensed from the downstream end. The venous filter circumferentially surrounds the bowl, with the bowl and the venous filter combining to define a venous chamber. The venous defoamer is at least partially disposed within the venous chamber, and is longitudinally spaced above the floor surface. Finally, the cardiotomy filter is stacked above the venous filter. With this construction, the reservoir is compact, and thus highly amenable to low volume applications, such as pediatric applications. Further, in some embodiments, the defoamers are located such that only cardiotomy blood foam contacts the cardiotomy defoamer, and only venous blood foam contacts the venous defoamer.

Yet other aspects in accordance with the present disclosure relate to a method for collecting and treating blood from venous and surgical site sources during a surgical procedure. The method includes directing venous source blood into an increasing diameter lumen of a downtube having a downstream end. The venous blood is dispensed from the downstream end to a floor surface of a bowl, the floor surface defined by an annular shoulder segment, an intermediate segment, and a protrusion. The shoulder segment circumferentially surrounds, and is radially spaced from, the downstream end, but is spatially located above the downstream end. The intermediate segment extends radially inwardly and downwardly from the shoulder segment to a bottom face that is spatially below the downstream end. The protrusion extends radially inwardly and upwardly from the bottom face to a center that is aligned with the lumen yet spaced below the downstream end. With this in mind, the venous blood experiences a smooth flow in travelling from the downstream end to the center, and from the center to the shoulder segment, in a manner that minimizes turbulence to reduce blood trauma and improve air handling (e.g., substantially laminar flow). The venous blood is guided from the shoulder segment through a venous filter and into a main chamber of a reservoir. Finally, cardiotomy blood from a surgical site source is directed through a cardiotomy filter and into the main chamber. In some embodiments, the surgical procedure is a pediatric surgical procedure and the main chamber is sized to establish a maximum flow rate of 2.2 liters/minute.

BRIEF DESCRIPTION OF THE DRAWINGS

FIG. 3A is a cross-sectional view of a portion of the reservoir of FIG. 1A, including a turret;

FIG. 3B is a top view of the reservoir of FIG. 1A;

DETAILED DESCRIPTION

Figure 1B:
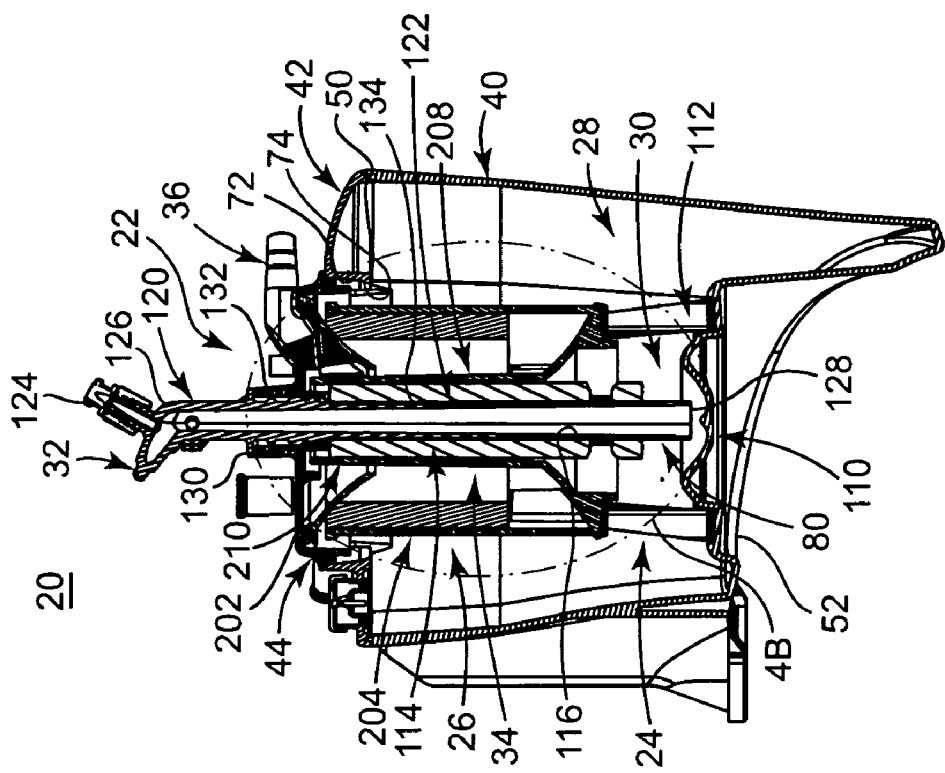
FIG. 1B is a longitudinal, cross-sectional view of the reservoir of FIG. 1A.
Figure 1A:
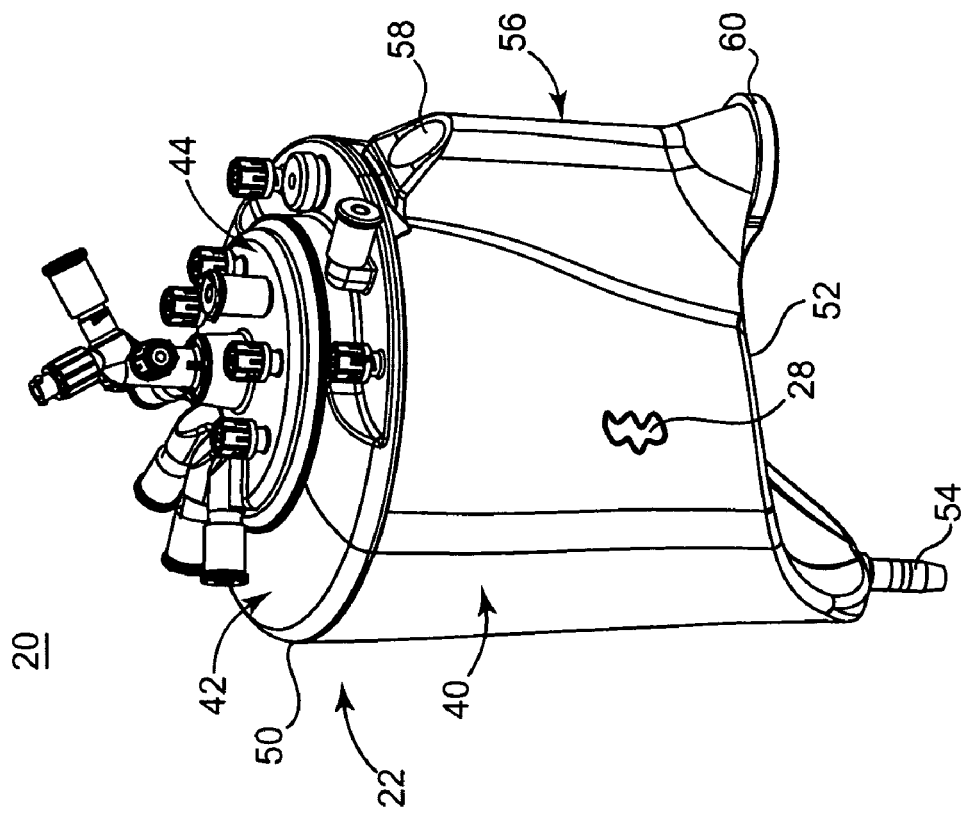
FIG. 1A is a perspective view of a cardiotomy and venous reservoir in accordance with principles of the present disclosure.

A cardiotomy and venous reservoir 20 in accordance with principles of the present disclosure is shown in FIGS. 1A and 1B. The reservoir 20 includes a housing assembly 22, a venous sub-assembly 24 (best shown in FIG. 1B), and a cardiotomy sub-assembly 26 (best shown in FIG. 1B). Details on the various components are provided below. In general terms, however, the housing assembly 22 defines a main chamber 28. The venous sub-assembly 24 is maintained by the housing assembly 22, and forms a venous chamber 30 through which venous blood flow from a venous inlet port 32 is directed into the main chamber 28. The cardiotomy sub-assembly 26 is also maintained by the housing assembly 22, and establishes a cardiotomy chamber 34 through which cardiotomy blood flow from one or more cardiotomy inlet ports 36 is directed into the main chamber 28. In this regard, the venous sub-assembly 24 is constructed to establish laminar flow of the venous blood to the main chamber 28, and the cardiotomy sub-assembly 26 is constructed to minimize trauma to the cardiotomy blood flow to the main chamber 28. The reservoir 20 is highly useful as part of a perfusion circuit, with particular applicability to patients in which relatively low volumes and flow rates are encountered (e.g., pediatric patients including neonates, infants, and children; small adults; etc.).

The housing assembly 22 can assume a variety of forms, and in some embodiments includes a housing 40, a lid 42, and a turret 44. The components 40-44 combine to define the main chamber 28, with the lid 42 and the turret 44 maintaining one or more ports, such as the cardiotomy inlet port(s) 36.

The housing 40 is a generally cylindrical body defining an upper side 50 and a lower side 52. The lid 42 is assembled to the upper side 50, with the lower side 52 optionally having a contoured shape and terminating at an outlet port 54 that is otherwise fluidly connected to the main chamber 28. In some constructions, and as best shown in FIG. 1A, the housing 40 forms a handle segment 56 in a region opposite the outlet port 54. The handle segment 56 is sized for convenient grasping by a caregiver's hand, and thus facilitates transporting of the reservoir 20. Further, the handle segment 56 is optionally configured to facilitate mounting of the reservoir 20 to a separate support structure (not shown), such as an upright post (e.g., IV stand). For example, a longitudinal passageway 58 is formed through the handle segment 56, with the handle segment 56 defining or including a shoulder 60 at the lower side 52. The passageway 58 is sized to slidably receive the post. The shoulder 60 serves as a support surface for maintaining the reservoir 20 relative to a corresponding feature of the separate support structure. Alternatively, the handle segment 56 can assume a variety of other forms, and in some embodiments is omitted.

Figure 2:
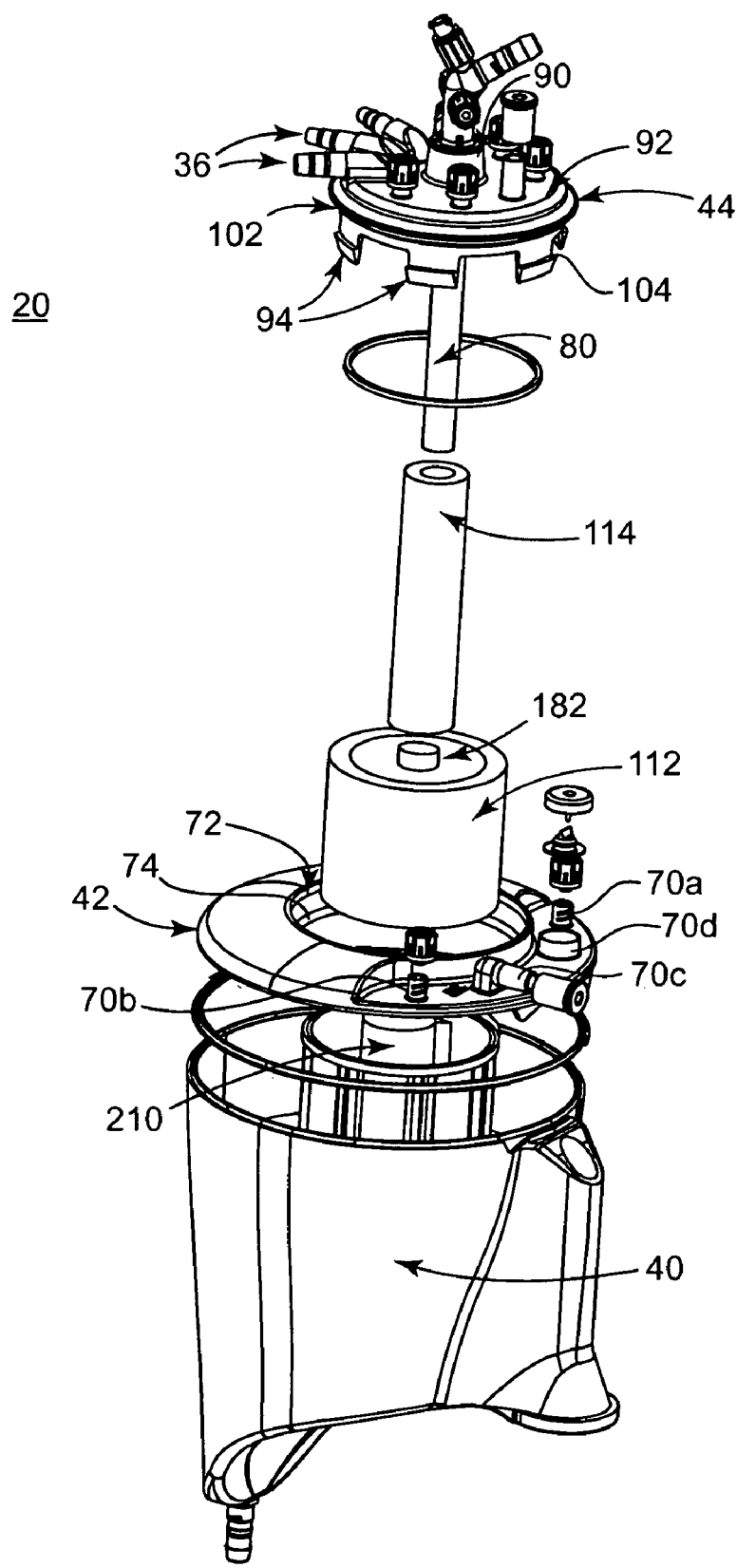
FIG. 2 is a perspective, exploded view of the reservoir of FIG. 1A.

With reference to FIG. 2, the lid 42 is mounted to (or alternatively formed as part of) the housing 40, and maintains or defines one or more connectors 70. For example, in some constructions, the lid 42 forms or provides luer connectors 70a, 70b, a ventilation connector 70c, and a pressure relief valve housing connector 70d. Additional connectors can also be formed or provided with the lid 42 and/or one or all of the connectors 70a-70d can be omitted. Regardless, the lid 42 forms a central aperture 72 sized to rotatably receive the turret 44 as described below. In this regard, the central aperture 72 is circumscribed by a ridge 74 (best shown in FIG. 1B) optionally constructed to promote rotatable mounting of the turret 44 relative to the lid 42.

The turret 44 is shown in greater detail in FIG. 3A. As a point of reference, the view of FIG. 3A illustrates the turret 44 in isolation, along with a portion of the cardiotomy sub-assembly 26 (referenced generally) and a portion of the venous sub-assembly 24 (referenced generally). In particular, and as described in greater detail below, the venous sub-assembly 24 includes a downtube 80 that is otherwise rotatably maintained by the turret 44.

With the above in mind and with reference between FIGS. 2 and 3A, the turret 44 includes, in some embodiments, an inner hub 90, a base plate 92, and a plurality of fingers 94. The inner hub 90 forms a bore 96 sized to coaxially receive and maintain the downtube 80. The base plate 92 extends radially outwardly from the inner hub 90, and forms or maintains the cardiotomy inlet port(s) 36. In some embodiments, two or more of the cardiotomy inlet ports 36 are provided, for example, FIG. 3B illustrates the turret 44 as providing four of the cardiotomy inlet ports 36. Alternatively, any other number, either greater or lesser, is equally acceptable. Additional fluid connectors can further be formed or carried by the turret 44, such as a prime connector 98, a luer connector(s) 100, etc.

Returning to FIGS. 2 and 3A, the plurality of fingers 94 project longitudinally downwardly from the base plate 92 and are circumferentially spaced from one another. In some embodiments, a continuous outer hub 102 is longitudinally disposed between the base plate 92 and the fingers 94, and serves to facilitate a fluid tight assembly to the lid 42. Regardless, the fingers 94 are constructed to exhibit a radially outward bias in extension from the base plate 92, and forms a ledge 104. Upon assembly of the turret 44 within the central aperture 72 of the lid 42, each of the ledges 104 are biased into sliding engagement with the ridge 74 as shown in FIG. 1B. With this construction, then, the turret 44 is rotatable relative to the lid 42 (and thus the housing 40), with each of the ledges 104 sliding along the ridge 74, thereby maintaining the turret 44 relative to the lid 42. The lid 42 and/or the turret 44 can have constructions differing from those described above. For example, the rotational features are optional and can be omitted. In more general terms, the housing assembly 22 serves to establish the main chamber 28, as well as flow paths or ports for venous and cardiotomy blood to the reservoir 20 and a flow path or port of the treated blood from the reservoir 20.

Returning to FIG. 1B, the venous sub-assembly 24 includes the downtube 80, as well as a bowl 110, a venous filter 112, and a venous defoamer 114. The downtube 80 forms a lumen 116 fluidly connected to the venous inlet port 32. The bowl 110 is located to receive liquid (e.g., venous blood) dispensed from the downtube 80, and to direct the liquid toward the venous filter 112. Finally, the venous defoamer 114 is positioned to interface with any foam associated with venous blood accumulated with the bowl 110. More particularly, the bowl 110 and the venous filter 112 combine to define at least a portion of the venous chamber 30, with the venous defoamer 114 exposed to foam rising within the chamber 30.

The downtube 80 can assume a variety of forms, and in some embodiments is defined by an upstream region 120 and a downstream region 122. The lumen 116 extends through the regions 120, 122, with the upstream region 120 establishing a fluid connection to the venous inlet port 32. Additional ports, such as a venous sampling port 124, a temperature monitoring port, etc., can also be formed or provided. Further, the upstream region 120 can form or define one or more bends 126. Regardless, the downstream region 122 extends from the upstream region 120 and terminates at a downstream end 128 fluidly opposite the venous inlet port 32.

The downstream region 122 extends into the housing 40, and thus the main chamber 28. The downtube 80 can optionally form one or more features, such as a flange 130 and grooves 132, to facilitate rotatable mounting of the downtube 80 within the bore 96 of the lid 42. Regardless, upon final assembly of the reservoir 20, the downtube 80 defines a chamber segment 134 extending from the turret 44 to the downstream end 128, with the downtube 80 being entirely linear along the chamber segment 134 in some embodiments. As illustrated, the linear chamber segment 134 can extend through at least a majority of the height or depth of the main chamber 28.

Figure 4A:
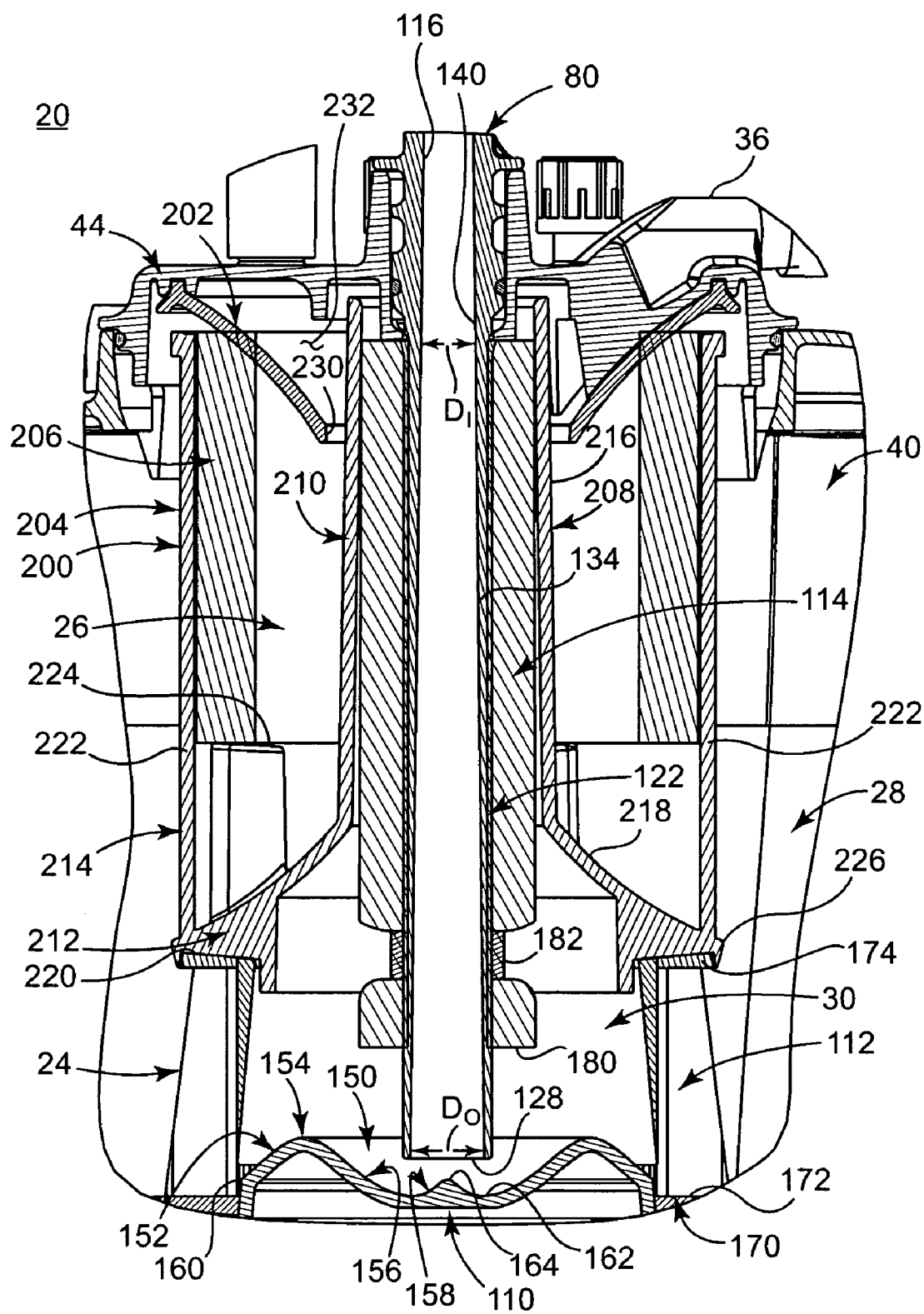
FIG. 4A is an enlarged, cross-sectional view of a portion of the reservoir of FIG. 1B, taken along the line 4A.

As best shown in FIG. 4A, the downtube 80 forms the lumen 116 as having an increasing in diameter or flaring to the downstream end 128. For example, relative to the chamber segment 134, the lumen 116 can be defined as having a chamber inlet side 140 adjacent the turret 44, with the chamber inlet side 140 defining a diameter $D_I$. The lumen 116 has a second diameter $D_O$ at the downstream end 128. With these designations in mind, the inlet diameter $D_I$ is less than the downstream or outlet diameter $D_O$ (e.g., the inlet diameter $D_I$ is on the order of 0.635 cm and the outlet diameter $D_O$ is on the order of 0.9525 cm in some embodiments), with the lumen 116 exhibiting a uniform increase in diameter from the inlet side 140 to the downstream end 128. In some embodiments, the lumen 116 uniformly increases in diameter along a majority of a length of the downtube 80; in other embodiments, the increase in lumen diameter is defined along an entirety of the downtube 80 length. Regardless, the flared lumen diameter slows the velocity of the venous blood being delivered through and along the lumen 116. This effect, in turn, reduces the velocity of bubbles impinging upon the venous filter 112 (as described below), as a buoyancy of the air bubble forces the air bubble to the free surface of the venous blood flow. As a result, air is removed from the venous blood flow more effectively such that the reservoir 20 exhibits improved air handling capabilities.

The bowl 110 is positioned to receive venous blood flow dispensed from the downstream end 128 of the downtube 80, and forms a floor surface 150. In some embodiments, the bowl 110 is an integrally formed component of the housing 40; alternatively, the housing 40 and the bowl 110 can be separately formed and subsequently assembled. The floor surface 150 serves to guide or direct venous blood flow within the venous chamber 30, such that the venous chamber 30 can be viewed as having an inlet at the downstream end 128 of the downtube 80 and an outlet at the venous filter 112.

A geometry of the floor surface 150 is selected to provide laminar flow transition from the downtube 80 to the venous filter 112. For example, and with additional reference to FIG. 4B (that otherwise illustrates the bowl 110 in isolation), the floor surface 150 is defined by a rim segment 152, an annular shoulder segment 154, an intermediate segment 156, and a protrusion 158. The rim segment 152 extends radially outwardly and downwardly from the shoulder segment 154, terminating at an outer edge 160. As described below, the outer edge 160 is positioned immediately adjacent the venous filter 112. The shoulder segment 154 defines an uppermost side of the floor surface 150 (upon final construction of the reservoir 20 and relative to the upright orientation of FIG. 4A), and encircles the downstream end 128 of the downtube 80. In this regard, a diameter defined by the shoulder segment 154 is greater than an outer diameter of the downtube 80 relative to at least the downstream region 122 thereof. The intermediate segment 156 extends radially inwardly and downwardly from the shoulder segment 154. In some constructions, a transition of the floor surface 150 from the shoulder segment 154 to the intermediate segment 156 is a gentle curve. The intermediate segment 156 forms or defines a bottom face 162 opposite the shoulder 154, with the bottom face 162 effectively defining a lowermost side of the floor surface 150 (relative to the upright orientation of FIG. 4A).

The protrusion 158 extends radially inwardly and upward from the bottom face 162 of the intermediate segment 156, terminating at a center 164. The center 164 is a generally curved surface, and is spatially positioned above the bottom face 162. As described in greater detail below, the curved, raised nature of the protrusion 158, and in particular the center 164, facilitates laminar flow of liquids dispensed onto the center 164 to the intermediate segment 156. In some constructions, a height of the protrusion 158 (i.e., linear distance between the bottom face 162 and the center 164) is in the range of 0.065-0.105 inch; alternatively in the range of 0.075-0.095 inch; and in yet other constructions is 0.085 inch. Further, an outer diameter of the protrusion 158 can be on the order of 0.1-0.3 inch; alternatively 0.2 inch. Other dimensions are also acceptable.

Figure 4B:
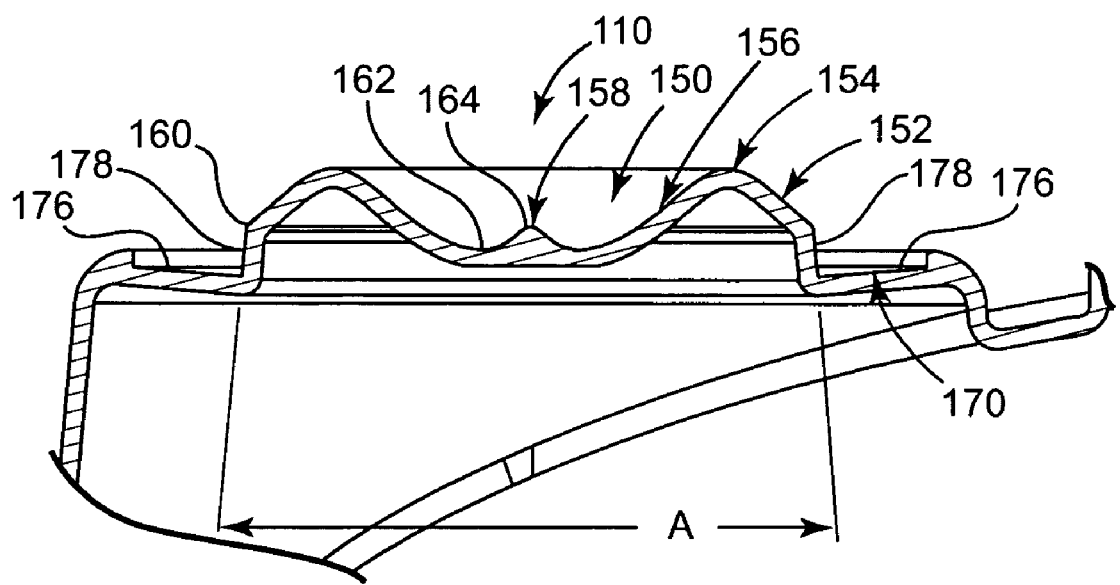
FIG. 4B is an enlarged, cross-sectional view of a bowl portion of the reservoir of FIG. 1A.

In some constructions, the bowl 110 further incorporates features that facilitate assembly of the venous filter 112. For example, the bowl 110 can form a trough 170 sized to receive and maintain the venous filter 112 immediately adjacent the outer edge 160 of the rim 152. In this regard, the venous filter 112 can assume a form commensurate with formats conventionally employed for venous blood filtering such as a screen material (e.g., 64 micron screen). With some constructions, the venous filter 112 is a pleated screen, formed as an annular ring having a first side 172 and a second side 174. With this but one acceptable configuration of the venous filter 112 in mind, the trough 170 is annular, and is defined in part (as best shown in FIG. 4B) by a base wall 176 and an inner wall 178. A width of the base wall 176 is commensurate with wall a thickness of the pleated venous filter 112. The inner wall 178 projects radially inwardly and upwardly from the base wall 176, and is configured to capture the first side 172 in an abutting-type relationship. The second side 174 is maintained by a portion of the cardiotomy sub-assembly 26 as described below. Alternatively, the venous filter 112 can be mounted relative to the bowl 110 in other ways and/or with additional components.

For reasons made clear below, the venous filter 112 can have a tapered shape, with the first side 172 defining an inner diameter greater than an inner diameter of the second side 174. The trough 170 is constructed to accommodate this tapered construction, with the inner wall 178 extending in an angular fashion from the base wall 176. For example, relative to the longitudinal cross-sectional view of FIG. 4B, opposing sides of the inner wall 178 define an included angle A in the range of 5°-15°, for example 10°, in extension from the base wall 176. Alternatively, the trough 170 can assume a wide variety of other forms, and/or may be formed apart from the bowl 110.

The venous defoamer 114 can be formed of a material conventionally employed for venous blood defoaming (e.g., polyurethane foam). In some embodiments, the venous defoamer 114 is sized for assembly about the downtube 80, and thus can have a generally tubular construction terminating at a leading end 180.

Upon final construction of the venous sub-assembly 24, the venous defoamer 114 is secured about the downtube 80 (e.g., via an elastomeric band 182), and the bowl 110 is positioned generally below the downstream end 128. Further, the venous filter 112 is secured within the trough 170. The bowl 110 is arranged relative to the downtube 80 such that the protrusion 158, and in particular the center 164, is axially aligned with a center axis of the lumen 116. The center 164 is vertically below and spaced from the downstream end 128 (e.g., a spacing on the order of 0.175-0.195 inch, alternatively 0.185 inch). Conversely, the shoulder segment 154 is spaced radially outwardly from the downtube 80, with the downstream end 128 being vertically below the shoulder segment 154. Finally, the leading end 180 of the venous defoamer 114 is horizontally above the shoulder segment 154, as well as the downstream end 128 (e.g., an offset distance on the order of 0.6 inch between the leading end 180 and the downstream end 128).

With the above construction, venous blood flow into the downtube 80 is directed by the lumen 116 to the downstream end 128. As described above, the flared nature of the lumen 116 serves to reduce a flow velocity of the venous blood as it flows to the downstream end 128. The venous blood is then dispensed from the downstream 128 and onto the floor surface 150 of the bowl 110. In this regard, the protrusion 158 disperses the venous blood flow radially outwardly from the center 164 and along the intermediate segment 156. Venous blood accumulates within the bowl 110, rising to a level of the shoulder segment 154. Because the downstream end 128 is "below" the shoulder segment 154, the downstream end 128 will also be within a volume of the accumulated venous blood so that prime within the lumen 116 is not lost even if venous blood flow to the downtube 80 is stopped. Regardless, the floor surface 150 directs the venous blood flow from the intermediate segment 158 and to the shoulder segment 154, and from the shoulder segment 154 to the rim segment 152. The rim segment 152, in turn, guides the venous blood flow to the venous filter 112 where appropriate filtration occurs prior to the venous blood entering the main chamber 28.

Figure 5:
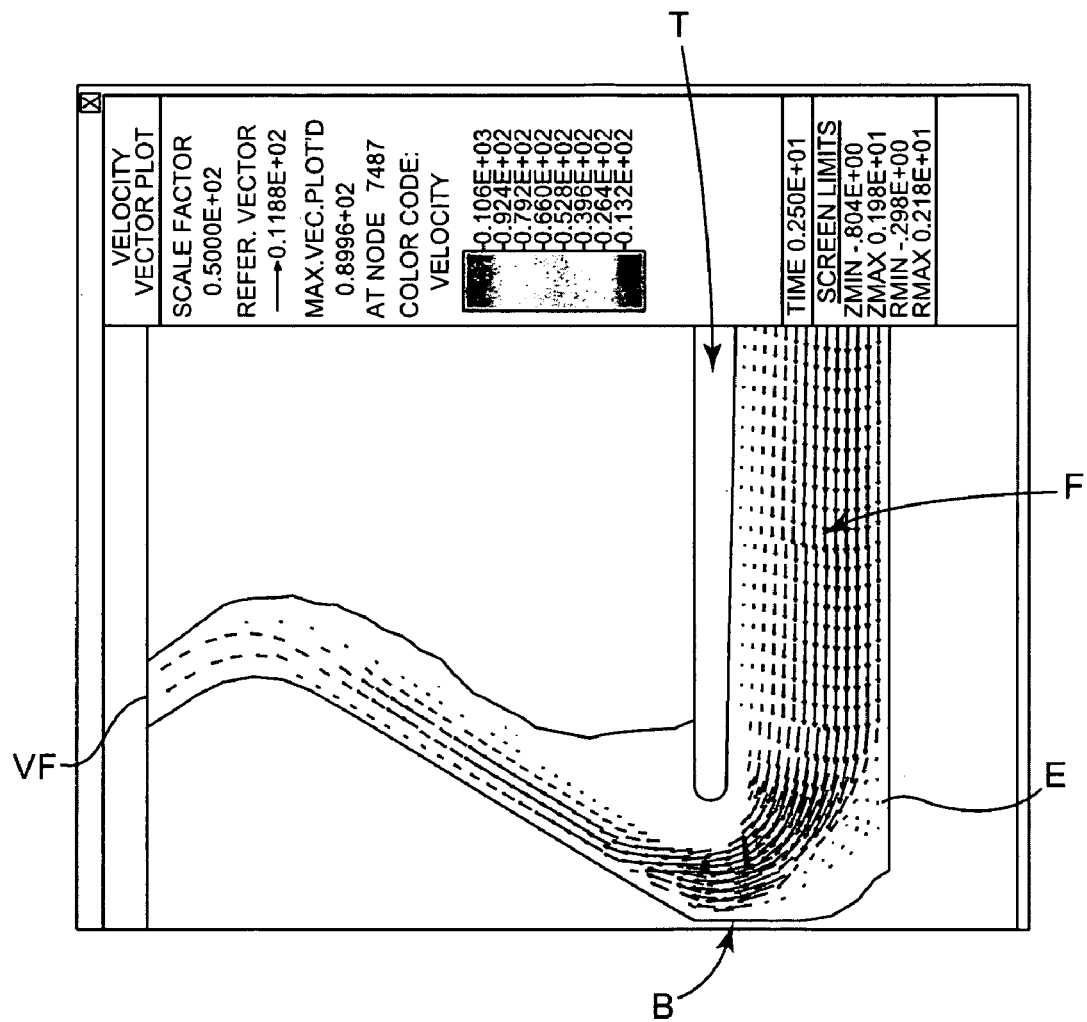
FIG. 5 is a CFD analysis relating to venous blood flow through the reservoir of FIG. 1A.

It has surprisingly been found that the desired laminar flow can be achieved and maintained by the downtube 80 and bowl 110 constructions of the present disclosure at the low flow rates typically encountered with pediatric cardiac surgery perfusion circuits. For example, FIG. 5 illustrates a screen shot of a computational fluid dynamic (CFD) analysis of venous blood flow F from a downtube T to a bowl B in accordance with the present disclosure. As a point of reference, the screen shot representation of FIG. 5 is rotated 90° to correspond with an upright orientation of a corresponding reservoir; further, only one-half of the flow is reflected (it being understood that flow to the "right half" of the flow shown is identical). The downtube T was constructed to have a flaring inner diameter lumen, with a downstream end E located vertically above a protrusion of the bowl B. The bowl B, in turn, incorporated the geometry and surface features described above (e.g., a protrusion height of 0.085 inch and diameter of 0.20 inch, and a spacing between the downstream end and the protrusion center of 0.185 inch). At flow rates on the order of 1.8 liters/minute, FIG. 5 illustrates that the flow F was smooth along an entirety of the bowl B, leading to the venous filter (identified generally at VF). This smooth flow is characterized as being substantially laminar (i.e., laminar flow or flow having a Reynold's number within 10% of laminar). As a point of reference, other constructions encompassed by the present disclosure incorporate substantially laminar, maximum flow rate characteristics that are greater or lesser than 1.8 liters/minute, as described below.

Returning to FIG. 4A, the leading end 180 of the venous defoamer 114 is offset from the above-described venous blood flow path such that the venous blood does not unnecessarily interface with the venous defoamer 114. Instead, any foam associated with the venous blood within the venous chamber 30 will rise upwardly (relative to the orientation of FIG. 4A) and only then contacts the venous defoamer 114 to effectuate desired defoaming. The non-foam portion of the venous blood, however, does not necessarily contact the venous defoamer 114. At elevated volumes, the venous blood level within the venous chamber 30 may rise to the venous defoamer 114, such that in some instances, at least some of the non-foam portion of the venous blood will contact the venous defoamer 114, while at least some of the non-foam portion (i.e., "below" the venous defoamer 114) will not.

The cardiotomy sub-assembly 26 is, in some embodiments, constructed in a stacked relationship relative to the venous sub-assembly 24. For example, in some embodiments, the cardiotomy sub-assembly 26 includes framework 200, a dish 202, a cardiotomy filter 204 (hidden in the view of FIG. 4A, but referenced generally), and a cardiotomy defoamer 206. In general terms, the framework 200 maintains the cardiotomy filter 204 and the cardiotomy defoamer 206. The dish 202 directs cardiotomy liquid flow from the cardiotomy inlet port(s) 36 to the framework 200, with the framework 200, in turn, directing the cardiotomy liquid flow to the cardiotomy filter 204 via a guide surface 208. The filtered cardiotomy liquid is subsequently directed to the main chamber 28 as described below. Further, the cardiotomy defoamer 206 is positioned to selectively interface with primarily the foamed portion of the cardiotomy liquid delivered to, and maintained by, the cardiotomy chamber 34.

The framework 200 can assume a variety of forms, and in some embodiments includes an inner post 210, a base 212, and an outer frame 214. The inner post 210 can be tube-like, sized to coaxially receive the downstream region 122 of the downtube 80 as well as the venous defoamer 114 (with embodiments in which the venous defoamer 114 is assembled over the downtube 80). Further, the inner post 210 forms a first section 216 of the guide surface 208, serving to direct cardiotomy liquid flow received from the dish 202.

The base 212 extends radially outwardly and downwardly from the inner post 210, and defines a second section 218 of the guide surface 208. In some constructions, the base 212 is adapted to maintain the second side 174 of the venous filter 112, and can form a corresponding trough 220. Thus, in some embodiments, the base 212 serves to additionally form a portion of the venous chamber 30, such that the framework 200 can be viewed as being part of the venous sub-assembly 24. Alternatively, however, the framework 200 can be a component entirely discrete from the venous sub-assembly 24.

The outer frame 214 extends from the base 212 opposite the inner post 210, and in some embodiments includes a series of spaced apart struts 222. The struts 222 maintain the cardiotomy filter 204 along an outer diameter collectively defined by the struts 222, and the cardiotomy defoamer 206 along a collectively-defined inner diameter. For example, the struts 222 can form a neck 224 (referenced generally) against which the cardiotomy defoamer 206 is received. In addition, the outer frame 214 defines an outlet section 226 of the guide surface 208. The outlet section 226 can be viewed as a portion of the cardiotomy filter 204, as a continuation of the base 212, can be a separate rim component, etc. Regardless, the outlet section 226 serves to direct cardiotomy liquid outwardly from the cardiotomy filter 204.

The cardiotomy filter 204 can be of a type conventionally employed for cardiotomy blood filtration and thus can be a felt material (e.g., 30 micron depth or mesh filter). In some constructions, the cardiotomy filter 204 is a pleated depth or mesh filter, formed as a ring and thus circumscribing the framework 200. Even further, the framework 200 is an integral component of the cardiotomy filter 204. Regardless, the cardiotomy filter 204 is positioned immediately adjacent the outlet section 226 of the guide surface 208.

The cardiotomy defoamer 206 is also of a type conventionally employed for cardiotomy liquid defoaming (e.g., polyurethane foam), and is assembled to the framework 200 so as to be spaced from the guide surface 208. For example, relative to the first section 216, the cardiotomy defoamer 206 is spaced radially outwardly from the guide surface 208. Relative to the second section 218 and the outlet section 226, the cardiotomy defoamer 206 is vertically above the guide surface 208. With this construction, and as described in greater detail below, flow of cardiotomy liquid along the guide surface 208 need not necessarily interface with the cardiotomy defoamer 206.

The dish 202 can have a funnel-like shape, and forms a central aperture 230. As shown in FIG. 4A, the dish 202 is configured for mounting to the housing assembly 22 (e.g., the turret 44), with a flow surface 232 of the dish 202 being fluidly open to the cardiotomy inlet port(s) 36 (best shown in FIG. 1A). The central aperture 230 is coaxially disposed about the inner post 210, with the flow surface 232 terminating in close proximity to the first section 216 of the guide surface 208. With this construction, then, the dish 202 directs cardiotomy liquid flow from the cardiotomy inlet port(s) 36 to the guide surface 208 via the flow surface 232/aperture 230.

Figure 6:
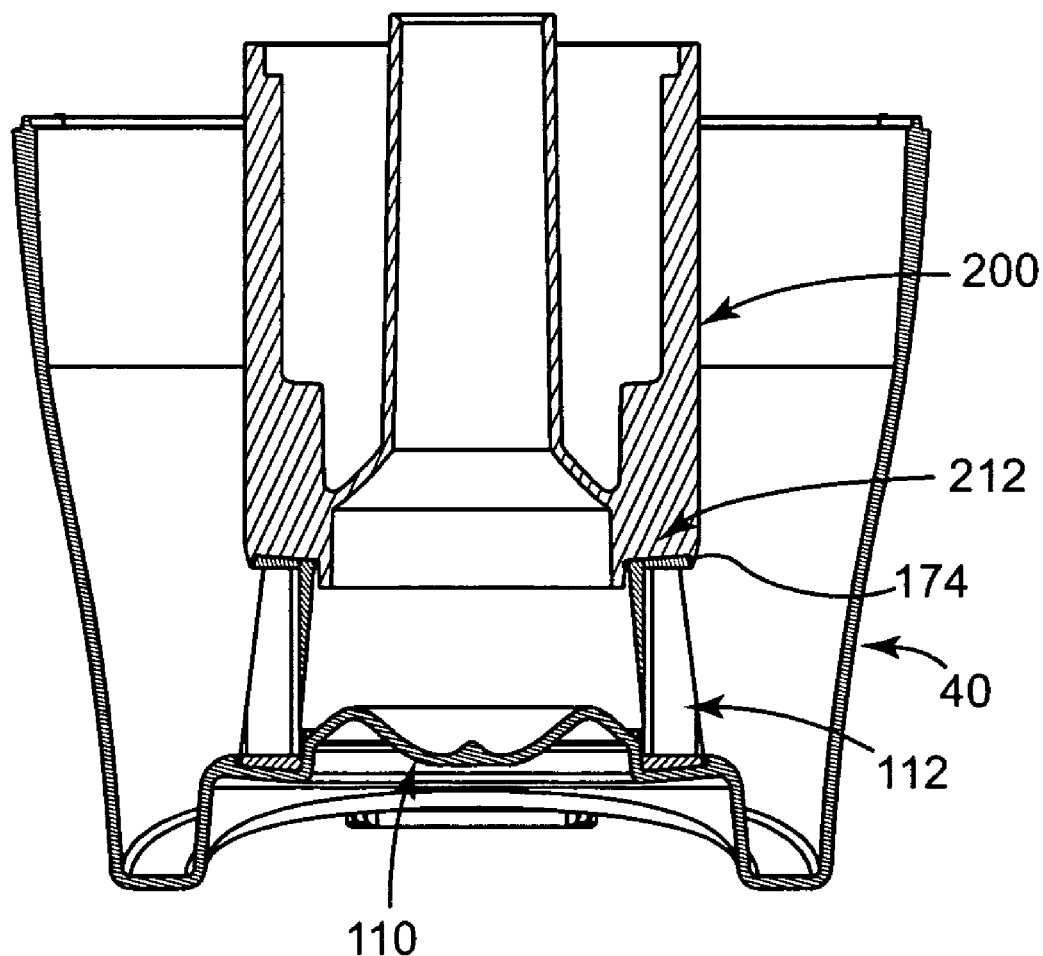
FIG. 6 is a cross-sectional view illustrating partial assembly of the reservoir of FIG. 1A.

In some embodiments, the cardiotomy sub-assembly 26 is mounted to and in conjunction with the venous sub-assembly 24. For example, FIG. 6 illustrates partial assembly of the reservoir 20, including the bowl 110 formed in or by the housing 40, and the venous filter 112 mounted to the bowl 110. The framework 200 is mounted to the venous filter 110, with the cardiotomy filter 204 being assembled to, or formed by, the framework 200. More particularly, the base 212 is mounted to the second side 174 of the venous filter 112. With reference to FIGS. 2 and 4A, the venous defoamer 114 is sandwiched between the downtube 80 and the inner post 210. The dish 202 is assembled about the inner post 210, for example by mounting of the dish 202 to the turret 44, followed by assembly of the turret 44 relative to the housing 40. Upon final construction, the inner post 210 and the cardiotomy filter 204 combine to at least partially define the cardiotomy chamber 34, with the guide surface 208 defining a flow path through the cardiotomy chamber 34.

More particularly, and with specific reference to FIG. 4A, cardiotomy liquid entering the reservoir 20 via the cardiotomy inlet port(s) 36 is directed by the dish 202 (via the flow surface 232) to the inner post 210. The cardiotomy liquid transfers from the dish 202 to the first section 216 of the guide surface 208 via the central aperture 230. The cardiotomy liquid flows (via gravity) along the first section 216 of the guide surface 208 to the second section 218, and then to the cardiotomy filter 204. Any foam associated with the cardiotomy liquid otherwise accumulating along the second section 218 "behind" the cardiotomy filter 204 rises upwardly and into contact with the cardiotomy defoamer 206. However, non-foamed portions of the cardiotomy liquid do not necessarily interface with the cardiotomy defoamer 206. At elevated volumes, a level of the non-foamed portion of the cardiotomy liquid can rise to the cardiotomy defoamer 206 such that at least some of the non-foamed portion contacts the cardiotomy defoamer 206, while at least some (i.e., non-foamed portion "below" the cardiotomy defoamer 206) does not. Regardless, the cardiotomy liquid is subsequently filtered by the cardiotomy filter 204.

With the one arrangement of FIG. 4A, following interface with the cardiotomy filter 204, the cardiotomy liquid is directed from the outlet portion 226 and onto the venous filter 112. More particularly, the cardiotomy filter 204 is located directly above the venous filter 112, with the filtered cardiotomy liquid flowing directly onto the venous filter 112. The venous filter 112, in turn, guides the cardiotomy liquid into the main chamber 28 for more complete mixing with the filtered venous blood. Thus, regardless of a volume of blood within the main chamber 28, cardiotomy blood flow from the cardiotomy filter 204 will not splash or "drip" into the main chamber 28; instead, a gentle, continuous flow to the venous filter 112 occurs, followed by flow into the main chamber 28.

The reservoir 20 provides a marked improvement over previous designs, and serves to gently and smoothly direct and combine the incoming flow of cardiotomy and venous blood. Venous blood flow to the venous chamber 30 and then the main chamber 28 experiences laminar flow even at low flow rates, with minimal or no splashing to the main chamber 28, and is continuously directed along smooth, curving surfaces. Similarly, cardiotomy liquid smoothly flows to the main chamber 28, and is minimally subjected to splashing-type actions. As a result, the reservoir 20 minimizes the opportunities for trauma-inducing events. The flow is smooth and controlled in order to minimize blood trauma and improve air handling.

The reservoir 20 is highly conducive to various perfusion applications, and in some embodiments is highly beneficial for small patients (e.g., neonates, infants, children, small adults, etc.). For example, at the flow rates and volumetric capacity typically associated with pediatric or small adult procedures (e.g., a main chamber 28 maximum volume on the order of 1,200 milliliters), substantially laminar flow of cardiotomy and venous blood through the reservoir 20 is substantially maintained. Further, the reservoir 20 minimizes the formation of air bubbles, yet is configured to readily remove formed air bubbles. The maximum flow rate supported by reservoirs of the present disclosure is, in some embodiments, highly useful with pediatric patients. In some embodiments, the reservoir 20 is sized to provide a maximum flow rate applicable to any pediatric category (neonate, infant, or child), and is on the order of 4.55 liters/minute. In other embodiments, the reservoir 20 is provided to a clinician in two or more different sizes, each with a different rated maximum flow rate. For example, a first neonate/infant reservoir having a rated maximum flow rate of 2.2 liters/minute; a second, pediatric/small adult reservoir having a rated maximum flow rate of greater than 1.8 liters/minute and less than 5.0 liters/minute; and a third, adult reservoir having a rated maximum flow rate of greater than 5.0 liters/minute (up to 7.0 liters/minute). As a point of reference, expected maximum flow rate parameters for pediatric patients (based on age, weight, and height) that are met by configurations of the present disclosure include: neonates (birth—one month) of 0.96 liters/minute; infants (one month—two years) of 1.83 liters/minute; and child/pediatric (two years—twelve years) of 4.55 liters/minute.

Figure 7A:
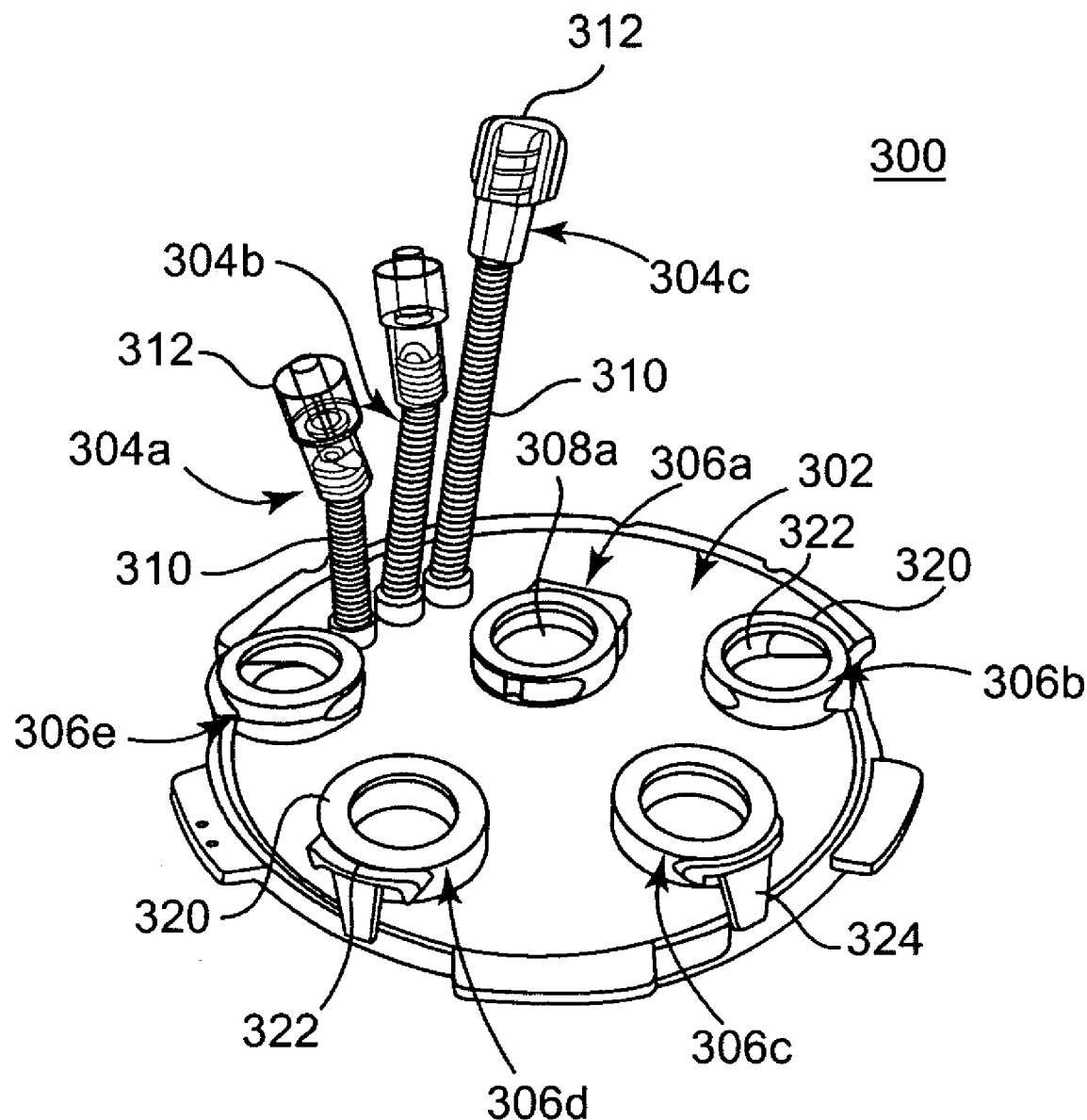
FIG. 7A is a top, perspective view of a cover assembly useful with the reservoir of FIG. 1A.

As indicated above, the reservoir 20 can include a wide variety of ports useful for facilitating desired connections within a perfusion circuit. As a point of reference, the design of small devices, such as the cardiotomy and venous reservoir of the present disclosure for pediatric applications, that provide all the connection sites and configurational flexibility required by different customers and different procedures is extremely challenging. Existing cardiotomy and venous reservoir devices typically have standard barb tubing connection sites, luer ports, and other sampling and monitoring sites crowded into spaces that are not ergonomically friendly. To address these concerns while still offering all desired connection sites, in some embodiments of the present disclosure, flexible, kink-resistant extensions and/or interchangeable connector mechanisms are employed. For example, FIG. 7A is a perspective view of a portion of a cover assembly 300 useful with an alternative reservoir (not shown) in accordance with the present disclosure. The cover assembly 300 can be assembled to the housing 40 (FIG. 1A) described above. With this in mind, the cover assembly 300 includes a cover 302, one or more extension connectors 304a-304c, and one or more snap-fit connector ports 306a-306e. As described below, the extension connectors 304a-304c and the snap-fit connector ports 306a-306e are fluidly open to a corresponding hole through a thickness of the cover 302 (e.g., FIG. 7A identifies hole 308a in the cover 302 and associated with the first snap-fit connector port 306a) so as to establish a fluid passageway to chamber(s) (not shown) encompassed by the cover 302 upon final placement of the cover assembly 300.

The extension connectors 304a-304c each include an extension body 310 and a port connector 312. The extension body 310 is a kink-resistant tubing (e.g., flexible tubing with a helically-wound spring disposed or embedded therewithin). In some embodiments, the port connector 312 is configured to receive and maintain a luer-type connection piece. With this construction, the extension connectors 304a-304c can be placed in very close proximity to one another (thereby conserving space along the cover 302) and can be readily articulated to a desired orientation by a user, thereby enhancing the ease with which connections to the reservoir (e.g., venous inflow, sampling, ventilation, temperature monitoring, cardiotomy inflow, etc.). Thus, though not fully depicted in the figures, the extension connectors 304a-304c can bend in any direction to provide a desired set-up orientation that might otherwise require rotational of an individual one of the extension connectors 304a-340c (e.g., venous inlet) or of the corresponding turret where provided (e.g., cardiotomy return line).

The extension connectors 304a-304c can be provided to a user apart from the cover 302 (e.g., as part of an accessory package) for subsequent assembly, or can be more permanently affixed. While three of the extension connectors 304a-304c are shown in FIG. 7A, in other configuration, a greater or lesser number are also acceptable.

The snap-fit connector ports 306a-306e can be generally identical, and each include a receptacle body 320 and a snap-fit connector mechanism 322. The receptacle body 320 can be cylindrically-shaped, and is sized to selectively receive a separate connector as described below. In this regard, the receptacle body 320 can be integrally formed with the cover 302 (e.g., as part of a molding process, resulting in the receptacle body 320 being defined as a raised column projecting outwardly from a major face of the corner 302) or can be separately formed and subsequently assembled to or within a corresponding hole (e.g., the hole 308a) in the cover 302.

Regardless of whether the receptacle body 320 is formed apart from the cover 302, the connector mechanism 322 is configured to facilitate releasable, fluid-sealed, snap-fit connection of a separate connector within the corresponding receptacle body 320 in a manner permitting the connector to rotate relative to the receptacle body 320. The connector mechanism 322 can include various components, such as a spring (not shown) and an actuator (e.g., the tab 324 identified in FIG. 7A for the third snap-fit connector port 306c) that are incorporated into the corresponding receptacle body 320 in some embodiments.

Figure 7B:
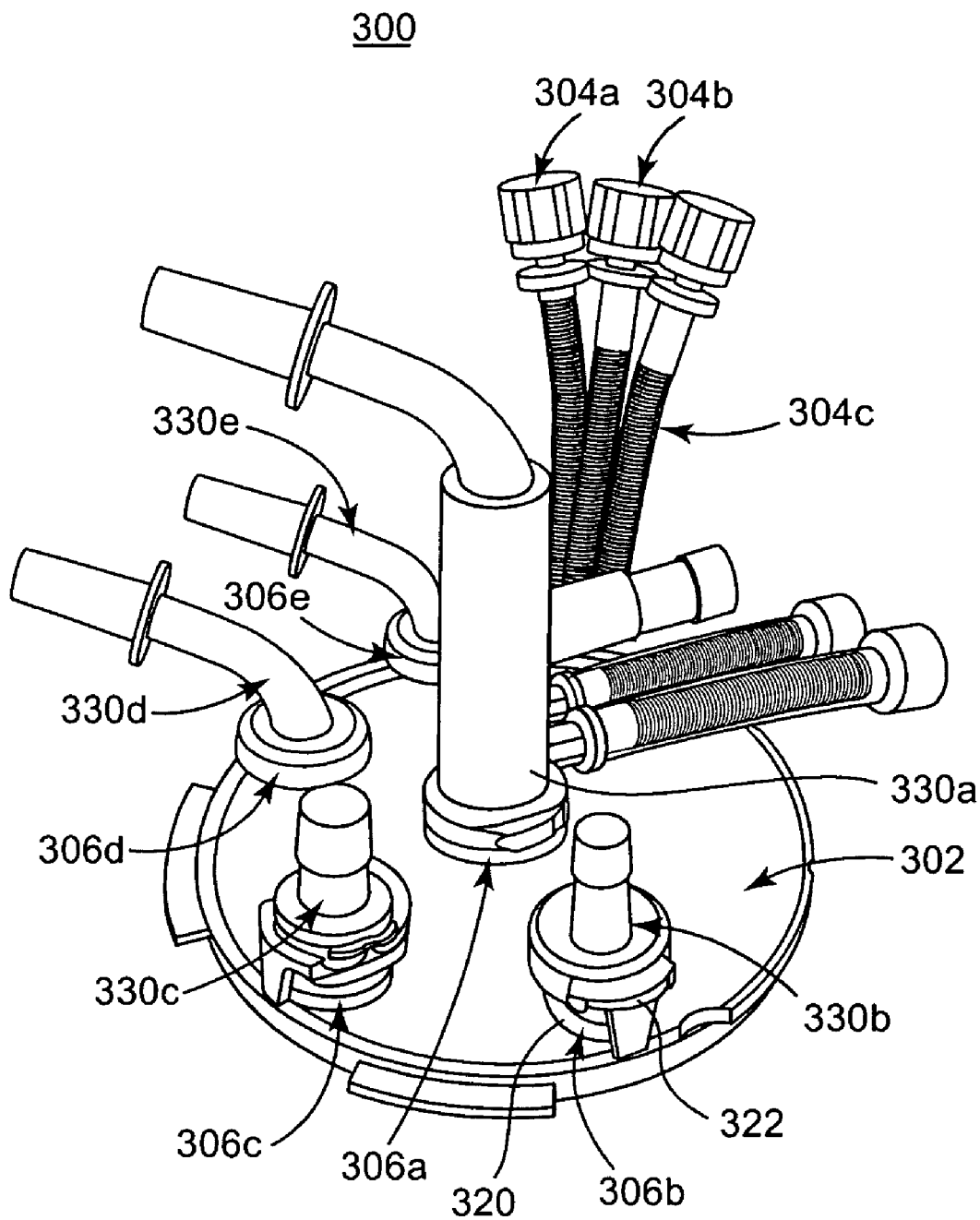
FIG. 7B is a top, perspective view of the cover assembly of FIG. 7A, including various connectors mounted thereto.

As shown in FIG. 7B, the cover assembly 300 allows for provision of wide variety connection devices that are ergonomically accessible and meet the needs of numerous end users. Alternatively, however, conventional connectors can be provided with the reservoir of the present disclosure.

The snap-fit connector ports 306a-306e are available for fluidly receiving (e.g., snap-fitting in place) an appropriate connector device 330a-330e (e.g., barbed connector, bent or curved tubing, etc.). With applications in which the end user does not require fluid interface with each of the connector ports 306a-306e, a cap may be snap-fitted to the corresponding, unused receptacle(s) 320 thereby conserving space. The optional snap-in-place connector ports 306a-306e provide an ability of each of the connectors 330a-330e to rotate independent of the others (i.e., the connector 330a can rotate within the receptacle body 320 of the corresponding snap-fit connector port 306a independent of the remaining connectors 330b-330e). This feature provides optimal flexibility in tube routing to and from the reservoir (not shown), and can replace the optional rotatable turret described above. Further, desired rotation of the connectors 330a-330e provides at least some strain relief for the corresponding connection site. Also, the snap-fit connector ports 306a-306e facilitate use of differently-sized tubing/adapters in conjunction with a desired blood handling system. As a point of reference, with many infant or other pediatric procedures, the same-sized reservoir will be used, but the corresponding tubing size will differ as a function of optimized prime volume relative to maximum required flow rates. With the optional, snap-fit connector ports 306a-306e of the present disclosure, separate adapters are not necessary to reduce or step-up the size of the tubing actually employed. Instead, a properly sized connector (not shown, but akin to the connectors 330b-330c) 306 can simply be assembled to the desired snap-fit connector port 306a-306e (e.g., interchanged with one of the existing connectors 330a-330e), and the tubing connected thereto.

In some embodiments, at least the connector mechanism 322 is "pre-connected" to the separate tubing (e.g., as part of the custom tubing pack) rather than provided directly with the cover 302. Regardless, because the connector mechanism 322 is not integrally molded to or with the cover 302, a user is afforded greater flexibility. For example, the cover assembly 300 can include the receptacle body 320 (or similar feature), with the separate tubing carrying the corresponding connector mechanism 322 for selective, rotatable assembly thereto. In related embodiments, the snap-fit connector port 306a-306e is affixed to the tubing and serves as the connector for releasable assembly to the cover 302 (e.g., the connector port 306a-306e serves as one of the connectors 330a-330e of FIG. 7B and is selectively assembled to a corresponding hole in the cover 302 (e.g., the hole 308a of FIG. 7A)).

Although the present disclosure has been described with reference to preferred embodiments, workers skilled in the art will recognize that changes can be made in form and detail without departing from the spirit and scope of the present disclosure. For example, while the snap-fit and the extension connectors have been described as being useful with a cardiotomy and venous blood reservoir, other extracorporeal devices in addition to reservoir can equally benefit. Thus, for example, the connectors can be employed with oxygenators, heat exchangers, pumps, etc. In more general terms, then, some aspects of the present disclosure relate to a perfusion device requiring fluid connection to one or more other components of a perfusion system and having a fluid connector assembly including a cover and at least one snap-fit, rotatable connector port removably assembled thereto. The perfusion device can include various other components useful for performing a perfusion procedure, such as a pump, filter, reservoir, oxygenator, heat exchanger, etc. Also, one or more flexible, kink-resistant extension connectors can be provided with the fluid connector assembly.

What is claimed is:

1. A cardiotomy and venous blood reservoir comprising:
a housing assembly forming a main chamber;
a cardiotomy inlet port fluidly connected to the main chamber;
a venous inlet port;
a downtube defining an upstream region, a downstream region, and a lumen extending therethrough, wherein:
the upstream region extends from the venous inlet port,
the downstream region extends from the upstream region and terminates at a downstream end located within the main chamber,
a diameter of the lumen increases along at least a portion of the downstream region to the downstream end; and
a bowl disposed within the main chamber and forming a floor surface facing the downstream end, the floor surface defined by:
an annular shoulder segment circumferentially surrounding and radially spaced from the downstream end, when the shoulder segment is spatially located above the downstream end,
an intermediate segment extending radially inwardly and downwardly from the shoulder to a bottom face opposite the shoulder, the bottom face being spatially located below the downstream end,
a protrusion extending radially inwardly and upwardly from the bottom face to a center, wherein the center is aligned with the lumen and spaced below the downstream end.

2. The reservoir of claim 1, wherein the increasing diameter of the lumen is exhibited along a majority of a length of the downtube in extension from the venous inlet port.

3. The reservoir of claim 1, wherein the chamber is defined by a height, and further wherein the downtube includes a chamber section having a length of at least one-half the height, and even further wherein the lumen increases in diameter along an entirety of the chamber section.

4. The reservoir of claim 1, wherein the housing assembly includes a cover, the venous inlet port projecting outwardly relative to the cover and the downtube forming a chamber section extending interiorly within the main chamber from the cover to the downstream end, and further wherein the lumen increases in diameter along an entirety of the chamber section.

5. The reservoir of claim 1, wherein a spacing between the center and the downstream end is in the range of 0.175-0.195 inch.

6. The reservoir of claim 1, wherein a height of the protrusion is in the range of 0.075-0.095 inch.

7. The reservoir of claim 1, wherein the floor surface forms a smooth curve in transition from the bottom face of the intermediate segment to the protrusion.

8. The reservoir of claim 1, wherein the intermediate segment continuously increases in diameter from the protrusion to the shoulder segment.

9. The reservoir of claim 1, wherein the floor surface is further defined by:
a rim segment extending radially outwardly and downwardly from the shoulder segment.

10. The reservoir of claim 9, wherein the floor surface is radially linear along the rim segment.

11. The reservoir of claim 10, further comprising:
a venous filter circumferentially surrounding and immediately adjacent the rim segment.

12. The reservoir of claim 1, further comprising:
a venous defoamer disposed about the downtube, the venous defoamer terminating at a leading end facing the bowl, the leading end being spatially positioned above the downstream end.

13. The reservoir of claim 12, further comprising:
a venous filter circumferentially surrounding the bowl, wherein the reservoir is constructed such that venous blood is directed through the downtube and into the main chamber via a flow path defined by the floor surface and the venous filter, and further wherein the venous defoamer is spaced from the flow path.

14. The reservoir of claim 1, further comprising:
a venous filter circumferentially surrounding the bowl to establish a venous chamber; and
a cardiotomy sub-assembly establishing a cardiotomy flow path from the cardiotomy inlet port to the main chamber, the cardiotomy flow path having an outlet side located above the venous filter.

15. The reservoir of claim 14, wherein the outlet side is fluidly associated with the venous filter such that cardiotomy liquid flow from the outlet side of the cardiotomy flow path travels along the venous filter and into the main chamber.

16. The reservoir of claim 15, wherein the venous filter increases in outer diameter from a first side to a second side, the outlet side of the cardiotomy flow path being positioned adjacent the first side.

17. The reservoir of claim 14, wherein the cardiotomy sub-assembly includes:
framework maintaining a cardiotomy filter and establishing a guide surface for directing flow of cardiotomy liquid from the cardiotomy inlet port, through the cardiotomy filter, and to the outlet side; and
a cardiotomy defoamer mounted to the framework at a location spaced from the guide surface.

18. The reservoir of claim 17, wherein the framework includes:
an inner post defining the guide surface and coaxially disposed over the downtube; and
an outer frame radially spaced from the inner post;
wherein the cardiotomy defoamer is mounted to the outer frame such that the guide surface extends below a lower end of the cardiotomy defoamer.

19. The reservoir of claim 18, further comprising:
a venous defoamer mounted between the downtube and the inner post.

20. The reservoir of claim 18, wherein the cardiotomy sub-assembly further comprises:
a dish having a flow surface open to the cardiotomy inlet port and extending to an aperture adjacent the inner post such that cardiotomy liquid from the cardiotomy inlet port flows along the flow surface and to the guide surface of the inner post via the aperture.

21. The reservoir of claim 1, wherein at least one of the inlet ports includes a snap-fit connector mechanism configured to interchangeably receive a separate fluid connector body.

22. The reservoir of claim 1, wherein the reservoir is configured for use with patients requiring low flow capacities, providing a maximum flow rate of 2.2 liters per minute, and a main chamber volume of not more than 1,200 milliliters.

* * * * *